United States Patent
Patt et al.

(10) Patent No.: US 7,952,056 B2
(45) Date of Patent: *May 31, 2011

(54) EXTENDED DYNAMIC RANGE LIGHT DETECTION SYSTEMS AND METHODS

(75) Inventors: Paul Patt, Danville, CA (US); Joel Talacki, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/701,337

(22) Filed: Feb. 5, 2010

(65) Prior Publication Data

US 2010/0133427 A1 Jun. 3, 2010

Related U.S. Application Data

(63) Continuation of application No. 11/774,938, filed on Jul. 9, 2007, now Pat. No. 7,683,299.

(51) Int. Cl.
*G01L 1/20* (2006.01)

(52) U.S. Cl. .............. 250/201.1; 250/208.2; 250/214 R; 356/318

(58) Field of Classification Search ............... 250/208.2, 250/208.1, 214.1, 214 R, 201.1, 226, 214 VT, 250/207, 330, 333; 356/318, 319, 417
See application file for complete search history.

(56) References Cited

U.S. PATENT DOCUMENTS

| | | | |
|---|---|---|---|
| 5,331,452 A | 7/1994 | Smyth et al. | |
| 5,381,250 A | 1/1995 | Meadows | |
| 5,608,063 A | 3/1997 | Hobbs, Jr. et al. | |
| 5,831,730 A | 11/1998 | Traina et al. | |
| 5,946,148 A | 8/1999 | Fischer | |
| 6,204,919 B1 | 3/2001 | Barshad et al. | |
| RE37,536 E | 2/2002 | Barnes | |
| 6,355,921 B1 | 3/2002 | Staton et al. | |
| 6,518,556 B2 | 2/2003 | Staton et al. | |
| 6,636,319 B1 | 10/2003 | Auth et al. | |
| 6,657,714 B2 | 12/2003 | Almogy et al. | |
| 6,806,460 B2 | 10/2004 | Corson | |
| 6,870,166 B2 | 3/2005 | Curry et al. | |
| 6,950,196 B2 | 9/2005 | Fielden et al. | |
| 7,211,778 B1 | 5/2007 | Smith et al. | |
| 2004/0206898 A1 | 10/2004 | Ratliff et al. | |
| 2005/0093796 A1 | 5/2005 | Fergason | |
| 2007/0121110 A1 | 5/2007 | Kralik et al. | |
| 2007/0138414 A1 | 6/2007 | Stevens et al. | |

*Primary Examiner* — Francis M Legasse, Jr.
(74) *Attorney, Agent, or Firm* — Kilpatrick Townsend & Stockton LLP

(57) ABSTRACT

Systems and methods for detecting and measuring light emitted from a sample and having a large dynamic range, e.g., a range of luminous intensity covering six or more orders of magnitude, that may be difficult to fully detect using a single detector with a limited detection range. Simultaneous measurements of the emitted light in two intensity ranges are performed using two detectors, e.g., one including a photomultiplier tube (PMT) and the other including a solid state detector such as a photodiode. A beam splitting element directs light emitted from a sample under investigation to both detectors simultaneously such that a portion of the light impinges on the first detector and a second portion of the light impinges on the second detector. A processor receives output signals from the two detectors and provides an output representing the luminous intensity of the sample over a detection range greater than the detection range of each individual detector, thereby providing a detection system having an enhanced dynamic range.

20 Claims, 2 Drawing Sheets

EXTENDED DYNAMIC RANGE LIGHT DETECTION SYSTEMS AND METHODS

CROSS-REFERENCES TO RELATED APPLICATIONS

This application is a continuation of prior application Ser. No. 11/774,938, filed Jul. 9, 2007 (Notice of Allowance issued Nov. 6, 2009), hereby incorporated by reference in its entirety for all purposes.

BACKGROUND OF THE INVENTION

The present invention relates generally to systems and methods for detecting light, and more particularly to systems and methods for large dynamic range light detection.

It is often desirable to detect (and possibly quantify) light emitted from light emitting samples or substances. Such detection capability is useful in various assays, such as, for example, DNA sequencing assays where different fluorescent substances may be attached to different amino acids. For certain assays it is also desirable to quantify the light emitted by a sample. However, light emitted by a light emitting sample, such as a sample containing a fluorescent substance, may be in a 6 decade ($10^6$) range of intensity for a given stimulation intensity. Samples may be distributed over an area that is stimulated by a stationary or scanned point light source of a single color, with the emitted light directed to a point optical detector, and the detector's electrical output quantized to a digital value representing the optical power detected in a given time interval. The set of values may be organized into a 2-dimensional array representing fluorescent emission over the sample area, where a given sample detection time corresponds to a given point in the sample area. Alternatively, the data may be collected serially, in time, and arranged in any way that correlates a particular sample with a particular reading.

In certain applications requiring an optical detection power range of roughly 0.3 pW to 300 nW, for example, and the requirement of a signal-to-noise ratio of about 10 at 50 pW in a time interval of 5 µs, a PMT (photomultiplier tube) detector must be used. The PMT's practical dynamic range for this time interval is between 3 and 4 decades, limited at the low end by signal-to-noise and at the high end by PMT anode current rating. The PMT gain may be adjusted for 300 nW at maximum anode current but 0.3 pW will not be detected, or for usable signal-to-noise at 0.3 pW but 300 nW will be above the PMT anode current rating. In prior art implementations, multiple scans with different stimulation intensities or PMT responsivities were required to be carried out for 6 decade detection, consuming extra time and possibly degrading the sample due to increased light exposure.

Therefore it is desirable to provide systems and methods that overcome the above and other problems.

BRIEF SUMMARY OF THE INVENTION

The present invention provides systems and method for detecting and measuring light emitted from a sample and having a large dynamic range, e.g., a range of luminous intensity covering six or more orders of magnitude, that may be difficult to fully detect using a single detector with a limited detection range.

In certain embodiments, simultaneous measurement of the emitted light in two intensity ranges is performed using two detectors, one including a photomultiplier tube (PMT) and the other including a solid state detector such as a photodiode. A beam splitting element directs light emitted from a sample under investigation to both detectors simultaneously such that most of the light impinges on the PMT and a smaller portion of the light impinges on the solid-state detector. A processor receives output signals from the two detectors and provides an output representing the luminous intensity of the sample over a detection range greater than the detection range of each individual detector, thereby providing a detection system having an enhanced dynamic range (ratio between maximum and minimum detectable light). In certain aspects, for example when the detection system is used in a scanning detection system, the processor scales and combines data from each detector into one data value per sample acquisition time with a continuous dynamic range of at least six decades (six orders of magnitude).

According to one embodiment, a scanning fluorescence detector system is provided that stimulates a sample point with light of a single color at a given instant in time, and a single intensity over the total scan area, and which detects emitted light using two detectors and a beamsplitter. The beamsplitter directs most of the light to a first detector element, such as a PMT, which detects the lower power range and directs the rest of the light to a second detector element such as a solid-state sensor, typically an APD (avalanche photodiode) or a PIN or PN (positive-intrinsic-negative, positive-negative) photodiode, which detects the higher power range. The responsivity of the detectors and the beamsplitter ratio are chosen so that the detected light will always be within the dynamic range of at least one of the two detectors.

Embodiments of the invention advantageously allow an area containing fluorescent samples of a given (emission) color to be scanned only once for all available data. A uniform scan intensity helps ensure uniform photobleaching for minimal effect on subsequent scans with the same color. This uniform exposure also has the benefit of not requiring linearity in response of the sample (i.e., the light-to-response of the sample itself is not required to be linear). This has advantages in systems containing mixtures or in samples where the linearity of response is not valid, or even known. Signal and data processing provide a data set representative of a single detector with 6 decades of dynamic range. In one aspect, data from only one detector may be taken, for example, where it is known a priori that the dynamic range of emitted light will be within the detection range of a single detector.

According to one aspect of the present invention, a light detection system with large dynamic range detection capability is provided. The system typically includes a first light detection element capable of detecting incident light over a first intensity range, and a second light detection element of a different type than the first light detection element, wherein the second light detection element is capable of detecting incident light over a second intensity range different than the first intensity range. The system also typically includes a beamsplitting element configured to transmit a first portion of incident light from a light emitting sample to the first light detection element and direct a second portion of the incident light to the second light detection element, wherein the first and second light detection elements simultaneously detect the incident light from the sample.

According to another aspect of the present invention, a method is provided for detecting light emitted from a sample using a detection system proximal to the sample. The detection system typically includes a beam splitting element configured to transmit a first portion of incident emitted light to a first detector element and to direct a second portion of the incident emitted light to a second detector element, wherein the first detector element is of a different type than the second detector element. The method typically includes the steps of simultaneously detecting the first portion of the emitted light with the first detector and detecting the second portion of the emitted light with the second detector, and providing output signals from each of the first and second detectors, each output signal representing a dynamic range that is different from the other. The method further typically includes processing the output signals from the first and second detectors to produce a combined output signal representing a dynamic range greater than the dynamic range of each of the detector output signals.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides wide dynamic range light detection systems and methods using two (or more) detectors in which part of the received light is directed to a low intensity light sensor, and part of the light is directed to a high intensity light sensor. The sensor outputs are merged into a single output representing the luminous intensity of the sample over a detection range greater than the detection range of each individual detector.

Figure 1:
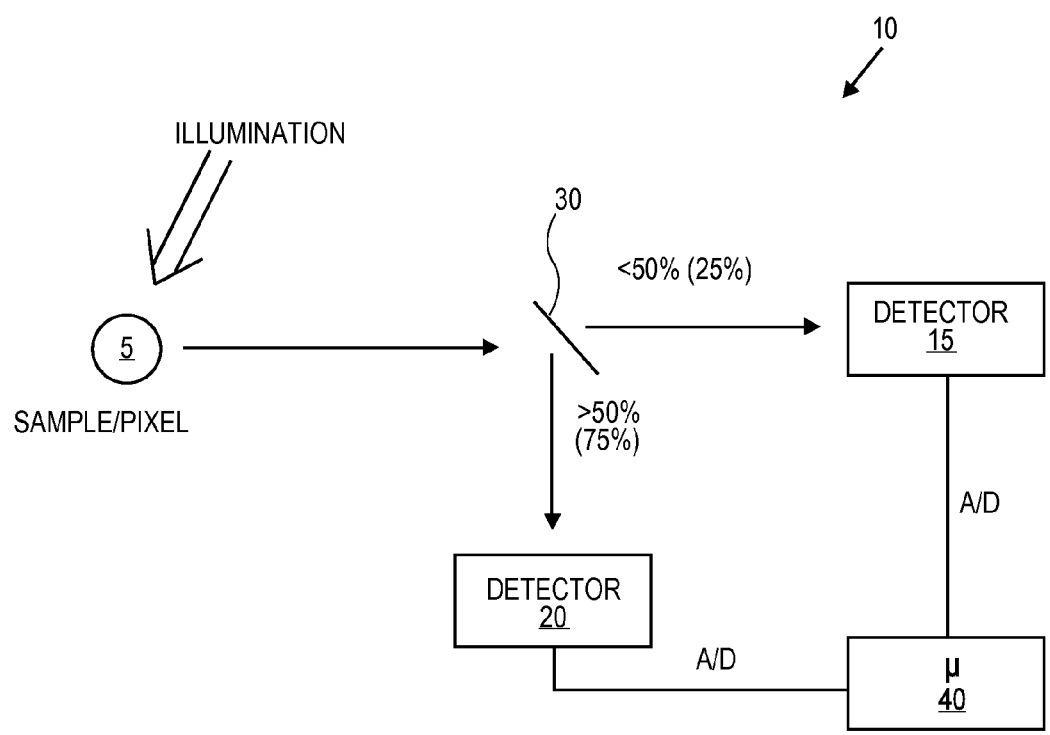
FIG. 1 illustrates a light detection system according to one embodiment.

According to one embodiment as shown in FIG. 1, a light detection system 10 includes a first detector 15, a second detector 20 and a beamsplitting element 30 configured to direct a portion of the light emitted from a sample 5 toward detector 20 and to allow a portion of the emitted light (e.g., photoluminescent emission such as fluorescent emission) to pass to detector 15. Sample 5 may be excited by illumination from a light source (not shown) such as a laser or other source of coherent or incoherent light. In a scanning system, for example, sample 5 may be illuminated with light of a single color at a given instant in time, and a single intensity over the total scan area. Useful light sources include lasers (e.g., gas lasers, diode lasers, excimer lasers, E-beam pumped lasers, etc.), arc lamps, LEDs, OLEDs, resonant phosphor structures, etc., or any light source having a suitable emission spectrum.

In one embodiment, the beamsplitter 30 is configured to direct most of the light to a first detector element configured to detect the lower power range, such as a photomultiplier tube (PMT) or other electro-optic detector having similar or equivalent range and signal-to-noise characteristics. Beamsplitter 30 is also configured to direct the remainder of the light to a second detector element configured to detect the higher power range, such as a solid-state sensor, typically a photodiode. Examples of useful photodiodes include an APD (avalanche photodiode) a PIN (positive-intrinsic-negative) photodiode, and a PN (positive-negative) photodiode. For example, in the embodiment as shown in FIG. 1, beamsplitter element 30 is configured to direct (e.g., reflect) most (i.e., >50%) of the light toward detector 20, which includes a PMT, whereas the remainder of the light is allowed to pass to detector 15, which includes a solid-state detector. Thus, in one embodiment, the ratio of light transmission vs. reflection of the beamsplitter is less than 1:1. In one specific embodiment, for example, beamsplitter 30 directs 75% of the light toward detector 20 and allows up to 25% of the light to pass to detector 15. It should be appreciated that detector 15 may include a PMT and that detector 20 may include a solid-state detector. In this case, the ratio of light allowed to pass versus the light directed/reflected by beamsplitter 30 should be greater than 1:1 so that most of the light passes to the PMT. In certain aspects, the beamsplitter ratio may vary from about 4:1 to about 1:4 depending, in part, on the positions of the low-power and high-power light detection elements relative to the beamsplitter. In certain aspects, the beamsplitter ratio may have values up to 1:10 or 1:20 or more. In certain aspects, the responsivity of the detection elements and the beamsplitter ratio are chosen so that the detected light will always be within the dynamic range of at least one of the two detection elements.

In one aspect, beamsplitter 30 includes an optically passive element such as a dichroic cube beamsplitter or other passive element(s). Beamsplitter 30, in certain aspects, includes an electro-optical device to facilitate adjustment of the beamsplitting ratio, e.g., under control of microprocessor 40, an external intelligence module, or by a user. It should also be appreciate that additional optical elements may be included to control (e.g., collect, steer and image) the emitted light and/or to condition the light. Such optical elements might include focusing lenses and pinholes (apertures) as may be commonly used in confocal microscopy systems.

Processor module 40 receives as input the output signals from detector 15 and detector 20. The signals from detectors 15 and 20 may be provided to microprocessor module 40 as analog or digital signals. In either case, in one aspect, an analog-to-digital (A/D) converter is used to convert the analog signals to digital signals for processing by microprocessor module 40. For example, microprocessor module 40 may include an A/D converter coupled with its input(s) and/or a detector may include an A/D converter coupled with its output. It should be appreciated that processor module 40 may include an intelligence module (e.g., processor executing instructions) resident in a data acquiring device or system such as a microarray scanner system, where the data signals (detector output) is provided to the intelligence module in real time as the signals are generated, or module 40 may be a separate stand alone system such as a desktop computer system or other computer system, coupled via a network connection (e.g., LAN, VPN, intranet, Internet, etc.) or direct connection (e.g., USB or other direct wired or wireless connection) to the acquiring device. The data signals may also be converted and stored in a memory unit or buffer or on a portable medium such as a CD, DVD, floppy disk or the like and provided to the intelligence module for processing after the experiment has been completed.

In one aspect, the signals from the two detectors are processed before conversion to digital data by pulse counters, current-to-voltage converters or charge integrators. Such processing may introduce a time delay that may be significantly different between the two detectors and which may need to be compensated for, either before or after conversion, so that a given sample time corresponds to a given point in the sample area to within a specific tolerance. In one aspect, therefore, the processor module 40 includes circuit elements to perform scaling and combining of the data from the two detectors into one data value per sample time with a continuous dynamic range of at least 6 decades, taking into account the differences in signal processing time delay and responsivity in the signal paths of the two detectors. The digital data is then processed into one data value per sample time with a continuous dynamic range of at least 6 decades. This may require color-dependent scaling as the detected color, and therefore the detector responsivities, may change from scan to scan. For example, in one aspect, digitized data values from the two detectors are stored in separate numerical arrays in the processor's memory with each value time-indexed. Data for the net detector responsivities is known from prior calibration and from the set beamsplitter ratio and detection wavelength and is stored in the processor. The time delay in each detector is also known from prior calibration and stored. Each detector has a defined and stored dynamic range corresponding to a minimum and maximum numerical value. A computing algorithm executed in the processor 1) adjusts the time indices for one or both of the arrays based on the calibration data for the closest practical delay matching, then 2) for each new time index chooses a value from the array within usable dynamic range, or the value nearest maximum if values from both arrays are within range, and 3) scales the chosen value with the matching responsivity calibration data to arrive at the final optical power value.

In some cases, the detection dynamic range is known or expected to be within the dynamic range of one of the detectors, in which case only data from that detector is taken. In these cases, in one aspect, the detector responsivity is adjusted electrically to match the expected dynamic range of the sample area.

In one aspect, a solid-state detector is used as a responsivity calibration reference for a PMT in the portion of the dynamic range where both detectors have linear responses. This requires that the responsivity of the solid-state detector has better stability with time and temperature than the PMT. For an APD, this would require a low APD gain or APD temperature stabilization.

Figure 2:
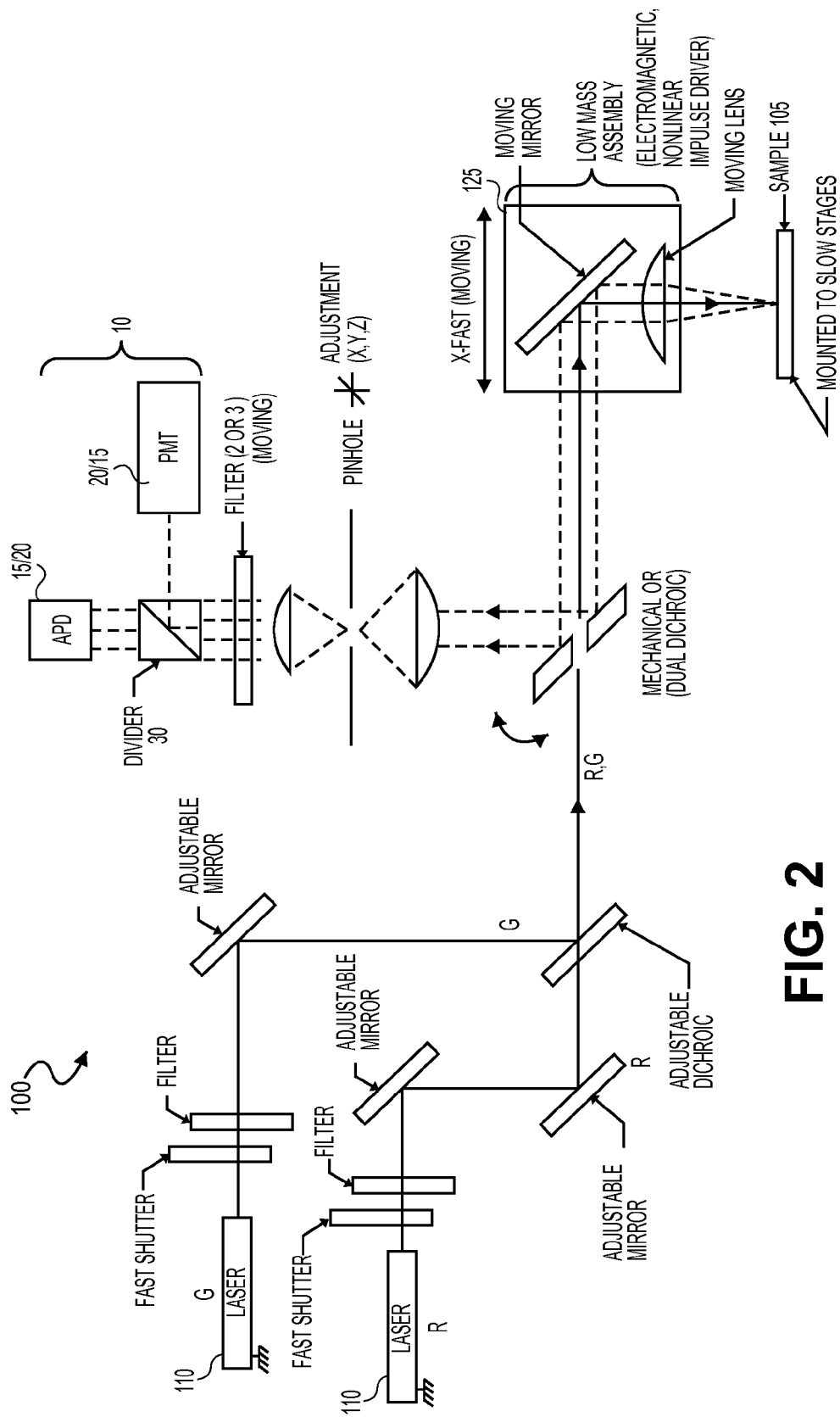
FIG. 2 illustrates a layout of the elements of a scanning detection system including a detection system of FIG. 1 according to one embodiment.

According to one embodiment, a method of light detection using a scanning fluorescence detector system includes positioning the detector system proximal to a sample or array of samples to be investigated, stimulating the sample area with a single color and a single intensity over the total sample area or scan area with a beamsplitter directing most of the detected light to a PMT and the rest of the light to a solid-state point detector, such as a photodiode or avalanche photodiode. One typical solid state detector is the Advanced Photonix P/N 012-70-62-541, 0.3 mm active area diameter avalanche photodiode. A typical PMT is a Hamamatsu R3896 PMT. The low-end light detector 20 can be any other detector with similar power range and signal-to-noise performance. In one aspect, a sample array is scanned sequentially, first with one color illuminating the sample area, then with another color, etc. FIG. 2 illustrates a layout of the elements of a scanning detection system 100 including a detection system 10 according to one embodiment. As shown, two excitation sources 110 provide excitation light to sample 105 (e.g., single sample, or array of samples) via scanning element 125. Scanning element 125 may include a scanning mirror and a lens coupled to a translation stage. Light emitted by the sample is reflected back and guided to detection system 10.

Embodiments of the invention advantageously allow an area containing fluorescent samples of a given color to be scanned only once for all available data. A uniform scan intensity helps ensure uniform photobleaching for minimal effect on subsequent scans with the same color. This uniform exposure also has the benefit of not requiring linearity in response of the sample (i.e., the light-to-response of the sample itself is not required to be linear). This has advantages in systems containing mixtures or in samples where the linearity of response is not valid, or even known. Signal and data processing provide a data set representative of a single detector with 6 decades of dynamic range. In one aspect, data from only one detector may be taken, for example where it is know a priori that the intensity range of a signal to be detected will be within the detection range of one of the detectors. In one aspect, the detector responsivity is adjusted to match the known or expected dynamic range of light emitted from the sample area.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A light detection system with large dynamic range detection capability, comprising:
   a first light detection element capable of detecting light over a first intensity range; and
   a second light detection element capable of detecting light over a higher intensity range than the first light detection element,
   wherein the first and second light detection elements are configured to simultaneously detect light from a light emitting sample, and an output signal from the second light detection element, capable of detecting light over the higher intensity range, is configured to be used as a feedback signal to modify an output of the first light detection element.

2. The system of claim 1, wherein a portion of the higher intensity range overlaps the first intensity range.

3. The system of claim 1, wherein the first light detection element is capable of detecting light over the first intensity range at a signal-to-noise ratio of greater than or equal to 10 at 50 pW in a time interval of 5 µs.

4. The system of claim 1, wherein the first light detection element includes a photomultiplier tube (PMT).

5. The system of claim 1, wherein the second light detection element comprises one of a photodiode, a PN photodiode, a PIN photodiode and an avalanche photodiode (APD).

6. The system of claim 1, further comprising:
   a beamsplitting element configured to transmit a first portion of light from the light emitting sample to the first light detection element and direct a second portion of the light to the second light detection element.

7. The system of claim 1, further comprising a processor module configured to receive and combine output signals from both the first and second light detection elements and to provide a composite output signal having a dynamic range that is greater than the dynamic range of the individual output signal of each of the first and second detection elements.

8. The system of claim 1, wherein the sample includes a photoluminescent substance that emits light at a substantially discrete wavelength.

9. The system of claim 1, wherein the sample includes a fluorescent substance.

10. The system of claim 1, wherein the second light detection element includes a solid-state detection element, such that an output signal from the solid-state detection element, which is capable of detecting light over a higher intensity range than the first detection element, is configured to modify an output of the first light detection element.

11. The system of claim 6, wherein the beamsplitting element transmits or reflects greater than 50% of the light to one of the first or second detection elements and reflects or transmits the remaining light to the other detection element.

12. The system of claim 6, wherein the beamsplitting element comprises an electro-optical beamsplitting element adjustable by a microprocessor using the feedback signal from the second detection element such that a ratio of transmitted light to reflected light is adjustable.

13. The system of claim 7, wherein the processor compensates for a time delay between the first and second signals when producing the composite output signal.

14. The system of claim 7, wherein the system is a scanning detector system, and wherein the processor is configured to scale and combine the first and second output signals into a composite signal having one data value per time interval with a continuous dynamic range of approximately 6 orders of magnitude.

15. A method of detecting light emitted from a sample using a detection system proximal to the sample, wherein the detection system includes a first detection element capable of detecting light over a first intensity range and a second detection element capable of detecting light over a higher intensity range than the first detection element, the method comprising:
  simultaneously detecting a first portion of the emitted light with the first detection element and detecting a second portion of the emitted light with the second detection element;
  providing an output signal representing a first dynamic range from the first detection element;
  providing an output signal representing a second dynamic range from the second detection element, wherein the second dynamic range is higher than the first dynamic range;
  processing the output signals from the first and second detection elements to produce a combined output signal representing a dynamic range greater than the dynamic range of each of the detection element output signals; and
  using the output signal of the second detection element, capable of detecting light over the higher intensity range, as a feedback signal to modify the output signal of the first detection element.

16. The method of claim 15, wherein a portion of the higher intensity range overlaps the first intensity range.

17. The method of claim 15, wherein processing includes compensating for a time delay between the first and second signals when producing the combined output signal.

18. The method of claim 15, further comprising:
  adjusting an electro-optical beamsplitting element, configured to transmit a first portion of emitted light to the first detection element and to direct a second portion of the emitted light to the second detection element, using a feedback signal from the second detection element.

19. The method of claim 15, further comprising:
  calibrating the first detection element using the second detection element.

20. The method of claim 15, wherein the second light detection element includes a solid-state detection element, such that an output signal from the solid-state detection element, which is capable of detecting light over a higher intensity range than the first detection element, is configured to modify an output of the first light detection element.

* * * * *